United States Patent [19]

Kohri

[11] 3,969,507

[45] July 13, 1976

[54] METHOD OF PREVENTING AND TREATING THROMBOSIS

[75] Inventor: Hideaki Kohri, Tokushima, Japan

[73] Assignee: Otsuka Pharmaceutical Company Limited, Tokyo, Japan

[22] Filed: Nov. 11, 1974

[21] Appl. No.: 522,835

[30] Foreign Application Priority Data

Nov. 10, 1973  Japan.............................. 48-125930

[52] U.S. Cl. ............................................... 424/258
[51] Int. Cl.$^2$.......................................... A61K 31/47
[58] Field of Search.................. 424/258; 260/288 A

[56] References Cited
UNITED STATES PATENTS

| | | | |
|---|---|---|---|
| 3,351,525 | 11/1967 | Hodec............................ | 260/288 A |
| 3,514,459 | 5/1970 | Ritter et al...................... | 260/288 A |
| 3,813,399 | 5/1974 | Huber-Emden..................... | 424/258 |

*Primary Examiner*—Leonard Schenkman
*Attorney, Agent, or Firm*—Sughrue, Rothwell, Mion, Zinn & Macpeak

[57] ABSTRACT

A method of preventing and treating thrombosis comprising administering a therapeutically effective amount of 5-(hydroxy-3-t-butylamino)propoxy-3,4-dihydrocarbostyril having the formula

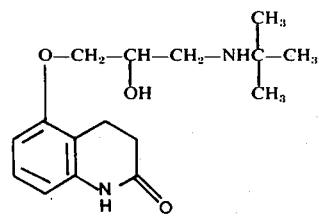

7 Claims, 4 Drawing Figures

METHOD OF PREVENTING AND TREATING THROMBOSIS

BACKGROUND OF THE INVENTION

1. Field of the Invention

This invention relates to a method for preventing and treating thrombosis. More particularly, this invention relates to a method for preventing and treating thrombosis in which the therapeutic agent is 5-(hydroxy-3-t-butylamino)propoxy-3,4-dihydrocarbostyril having the following formula

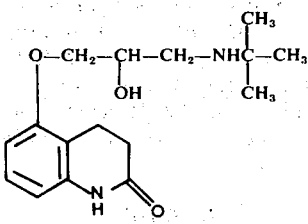

2. Description of the Prior Art

Hitherto, developments in medicine and pharmacy have contributed to the establishment of advanced therapeutic systems, whereby a number of serious diseases have been overcome. However, no effective and reliable therapeutic agent or method has yet been established for circulatory diseases, particularly, ischemic diseases, arteriosclerosis and cerebral thrombosis. Since these circulatory diseases are often fatal, development of promising agents for preventing and treating these serious diseases has been of great concern to many people. The cause of these diseases is considered to be thrombosis as described in Hovig, T.: "Platelet Adhesion and Aggregation in Thrombosis": *Countermeasures* (Mammen, E. F., Anderson, G. F. & Barnhart, M. I. Eds.), p. 137 (1970); Bizzozero, J.: *Virchows Arch.*, 90, 261 (1882); and Eberth, J. C. & Schimmelbusch, C.: *Virchows Arch.*, 103, 39 (1886).

Thrombus is a clot formed by a coagulation of blood flowing in a blood vessel and the origin of the formation of thrombus and the symptoms caused by the thrombus are called thrombosis. A thrombus is useful in that damaged parts of a blood vessel are reinforced and in that continuous bleeding due to the activity of blood platelets as a "trigger" is prevented. On the other hand, the thrombus has negative aspects in that the thrombus obstructs the blood vessel cavity or obstructs the blood vessels of organs, limbs and the like when it is transported to other organs by blood flow thereby causing an embolus infarction. Therefore, thrombi formed in the main organs such as the heart, lungs, brain and the like are accompanied by fatal effects such as cerebral infarction (embolus), myocardiac infarction and pulmonary infarction. Further, in other diseases such as diabetes, malignant tumors, essential hypertension, valvular cardiac disease, Basedow's disease, aorta syndrome mucous tumor and the like, thrombi tend to be formed secondarily and also easily develop due to changes in the nature of blood per se, for example, coagulation acceleration state, etc. and blood vessel wall (Sozo Matsuoka, *Factors for Bleeding and Thrombosis*, page 206, published by Kinbara Publishing Co., 1969 and Kaname Kotake, "Thrombus Formation and Platelets", *Metabolism and Disease*, Vol. 10, No.2, page 118, 1973).

Factors for thrombus formation include (1) change in the nature of the blood, (2) change in the blood flow and (3) change in blood vessel wall. Reference can be made to Tadashi Maekawa, *Ketsueki To Myakkan* (*Blood and Vessel*), Vol. 1, No. 4, pp 11–24, 1970. The normal flowing blood maintains an adequate dynamic balance between aggregation and dissociation of platelets as well as between coagulation and thrombolysis of the blood. Thrombosis can occur when this balance is lost due to stress or abnormal physiological conditions.

In recent years, the modern diet has very likely tended to induce arterioschlerosal disorders with a result in a possible increase in the occurrence of thrombosis. Under these circumstances, the development of chemo-therapeutics for treating and preventing thrombosis has been greatly desired. For thrombosis, it is more effective to prevent the formation of thrombi by inhibiting further development of thrombi. Disorders induced by the secondarily formed thrombi can also be improved by administering therapeutic agents for alleviating the thrombi in combination with therapy for the fundamental disease.

SUMMARY OF THE INVENTION

As a result of various investigations for the development of agents which are effective for preventing and treating thrombosis, it has now been found that 5-(hydroxy-3-t-butylamino)-propoxy-3,4-dihydrocarbostyril (hereinafter, referred to as OPC for brevity) having the formula

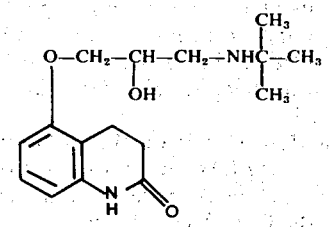

at low concentrations can specifically inhibit the aggregation of blood platelets.

It has been additionally found on further studies on OPC that this compound is very effective for preventing and treating thrombosis when OPC is administered orally or intravenously to mammals including humans.

This invention, therefore, provides a method for preventing blood platelet aggregation and minimizing blood platelet adhesion comprising applying in vitro or in vivo an effective amount of 5-hydroxy-3-t-butylamino(propoxy-3,4-dihydrocarbostyril) having the formula

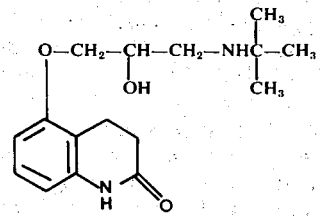

This invention, also provides a method for preventing and treating thrombosis comprising administering a therapeutically effective amount of 5-(hydroxy-3-t-butylamino)propoxy-3,4-dihydrocarbostyril to a subject needing same.

BRIEF DESCRIPTION OF ACCOMPANYING DRAWINGS

Figure 1:
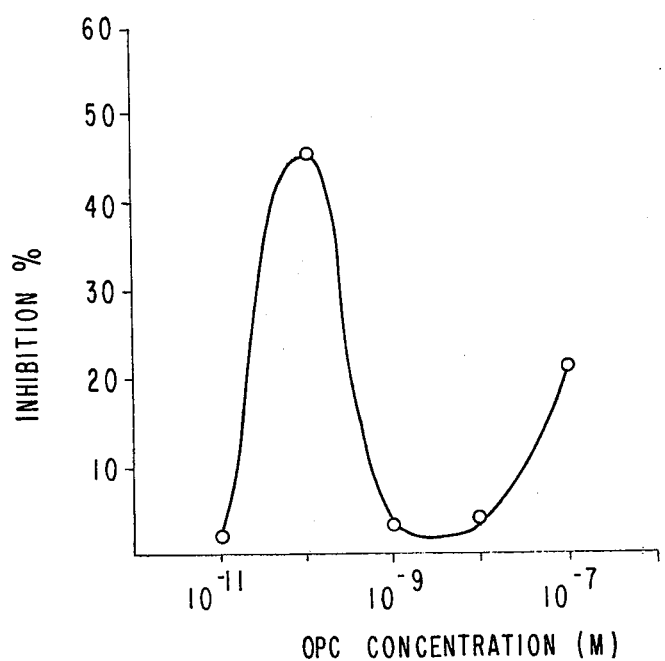
FIG. 1 shows the effect of OPC on ADP-induced platelet aggregation.

In FIG. 1 to 4, the abscissa represents concentrations of OPC and the ordinate represents the percent inhibition.

DETAILED DESCRIPTION OF THE INVENTION

The OPC compound used in this invention is known in the art as disclosed in, for example, Belgian Pat. No. 794,669. The acute toxicity ($LD_{50}$) of this compound in rats is 153 mg/Kg body weight in intravenous administration and 1400 mg/Kg body weight in oral administration.

The OPC exhibits a remarkable inhibitory effect in vivo on platelet aggregation induced by ADP (adenosine diphosphate) or collagen at extremely low concentrations such as $10^{-5}$ or $10^{-11}$ M. That is, this compound posesses a specific inhibitory effect on platelet aggregation and this pharmacological effect is illustrated in greater detail in the following Reference Example.

According to one aspect of the present invention, i.e., an application of the OPC compound in vivo, OPC is generally administered orally in a dosage of from about 5 to about 10 mg per subject per day. In determining the dosage, the severity of the conditions in the subject to be treated can be an important factor but the difference in the body weight of the subject appears to be immaterial.

A suitable dosage form for the oral administration is tablets comprising OPC and pharmaceutically acceptable carriers such as corn starch, crystalline cellulose, lactose and the like which are commonly used in pharmaceutical compositions.

In this Reference Example and in the Examples hereinafter described, all parts, percents, ratios and the like are by weight unless otherwise indicated.

REFERENCE EXAMPLE

Determination of Aggregation Property

Blood was drawn from a healthy male adult human into a syringe previously containing 3.8% sodium citrate in an amount of 1/10 volume of the blood drawn, and the blood was separated by centrifuging to obtain a platelet-rich-plasma (PRP) and a plasma containing no platelets. The PRP was then turbidimetrically analyzed using an aggregometer manufactured by Bryston Co. [Born, Nature, 194, 927-929 (1962) and O'Brien, J. Clin. Path., 15, 452–455 (1962)]. That is, to a 0.9 ml aliquot of the above obtained PRP sample was added either 0.1 ml of a physiological salt solution or an aqueous OPC solution having various concentrations to obtain a control sample and an experimental sample, respectively. Each of the resulting samples was then incubated for 1 minute, and thereafter, 0.1 ml of collagen (333 ± 12 μg/ml) or ADP (7.5 × $10^{-4}$ M) was added thereto. The maximum transmittance measured 8 minutes after the addition of the collagen or ADP was divided by the difference between the transmittance of the PRP and that of the plasma containing no platelets to determine the aggregation property.

Determination of Adhesiveness

A blood sample as prepared in the same manner as described above was analyzed to determine the adhesiveness of platelets in accordance with a modification of the method of A. J. Hellem et al, Scand. J. Haemat., 7, 374 (1970). That is, 1 ml of the blood sample was allowed to fall due to by gravity through a vinyl tubular column having an inside diameter of 3 mm and a length of 13 cm packed with glass beads. The difference between the number of platelets in the blood sample prior to passing through the column and that in the blood sample after passing through the column was divided by the number of platelets in the blood sample prior to passing through the column and the value obtained was taken as the adhesiveness of platelets. In this case, OPC or a physiological salt solution was previously added to the blood in an amount of 1/10 volume of the blood, and the resulting sample was incubated for 10 minutes before passing through the column.

The procedure for the determination used in each case will be described in greater detail in the examples hereinafter given.

EXAMPLE 1

The effect of OPC on ADP-induced platelet aggregation was evaluated as follows.

Blood was drawn from a healthy male adult human into a syringe previously containing 3.8% sodium citrate in a volume of 1/10 of the blood drawn. The blood was divided into two equal portions. One portion was centrifuged at a rate of 1000 rpm for 10 minutes, and the supernatant was taken for use as a platelet-rich-plasma sample. The other portion was centrifuged at a rate of 3000 rpm for 15 minutes, and the supernatant was taken for use as a platelet-poor-plasma (PPP) sample. A PRP sample containing about 300,000 platelets per μl of the sample was prepared by appropriately diluting the PRP sample obtained as above with the PPP sample. A 0.9 ml aliquot of the resulting PRP sample was placed in a cylindrical glass cell followed by the addition of 0.1 ml of an aqueous solution of OPC ($10^{-5}$ to $10^{-12}$ M). A steel stirrer was placed in the cylindrical glass cell and the cell was set in an aggregometer maintained at a temperature of 37°C. The mixture in the cell was preincubated at 37°C for 1 minute while stirring at a rate of 1,100 rpm. Then 0.1 ml of an aqueous solution of ADP having a concentration of 7.5 × $10^{-5}$ M as an aggregation inducer was added to the mixture and the transmittance of the mixture was determined. The rate of aggregation was represented in terms of the quotient obtained by dividing the maximum transmittance 8 minutes after the addition of ADP by the difference between the transmittance of the PRP sample and that of the PPP sample. The results obtained are shown in FIG. 1.

From FIG. 1, it can be seen that an OPC concentration of about $10^{-10}$ M exhibits an inhibitory effect on ADP-induced platelet aggregation.

EXAMPLE 2

The effect of OPC on collagen-induced platelet aggregation was evaluated in the same manner as described in Example 1 but using an aqueous collagen solution instead of the aqueous ADP solution as an aggregation inducing agent. The rate of aggregation was evaluated in the same manner as described in Example 1 and the results obtained are shown in FIG. 2.

Figure 2:
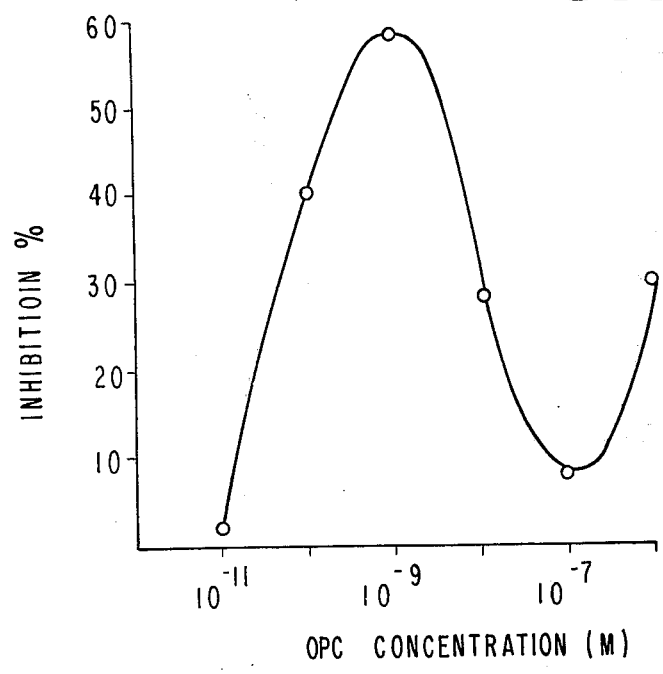
FIG. 2 shows the effect of OPC on collagen-induced platelet aggregation.

As shown in FIG. 2, an OPC concentration around $10^{-9}$ M exhibited an inhibitory effect on collagen-induced platelet aggregation.

EXAMPLE 3

The effect of OPC on platelet adhesiveness was evaluated as follows.

Blood was drawn from a healthy male adult human into a syringe previously containing 3.8% sodium citrate in an amount of 1/10 volume of the blood drawn. To a 0.9 ml aliquot of the blood was added 0.1 ml of an aqueous OPC solution having various concentrations or 0.1 ml of a physiological salt solution as a control. Each of the resulting samples was incubated at 37°C for 10 minutes and then allowed to fall through the same column as used in the Reference Example to determine the adhesiveness of the platelets, respectively. The results obtained on comparing the adhesiveness with the use of OPC and that with the use of the control are shown in FIG. 3.

Figure 3:
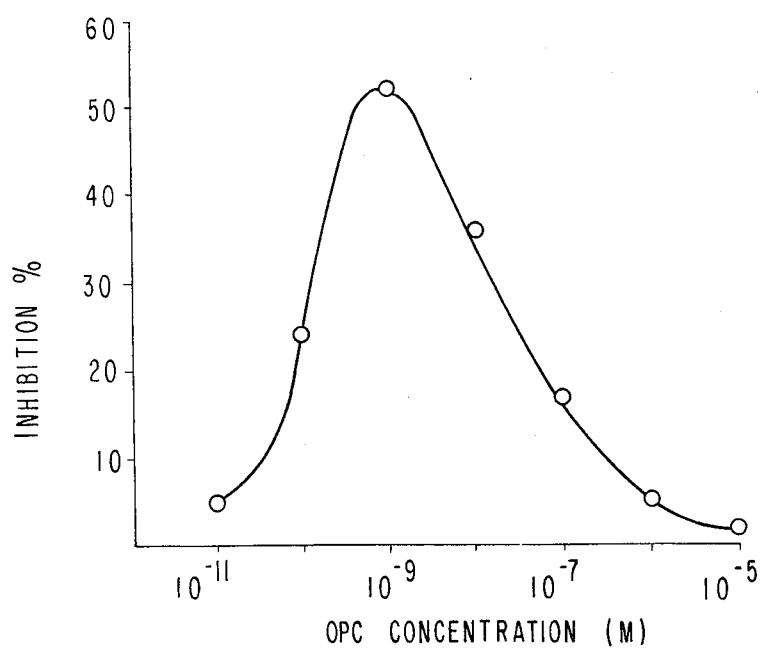
FIG. 3 shows the effect of OPC on platelet adhesiveness.

In FIG. 3, the percent inhibition exhibited a maximum at an OPC concentration of about $10^{-9}$ M.

EXAMPLE 4

The effect of OPC on platelet adhesiveness was evaluated in the same manner as described in Example 3 except that 0.1 ml of an aqueous adrenalin solution having a concentration of 5 γ/ml was added to the samples as an adhesiveness-inducing agent.

Figure 4:
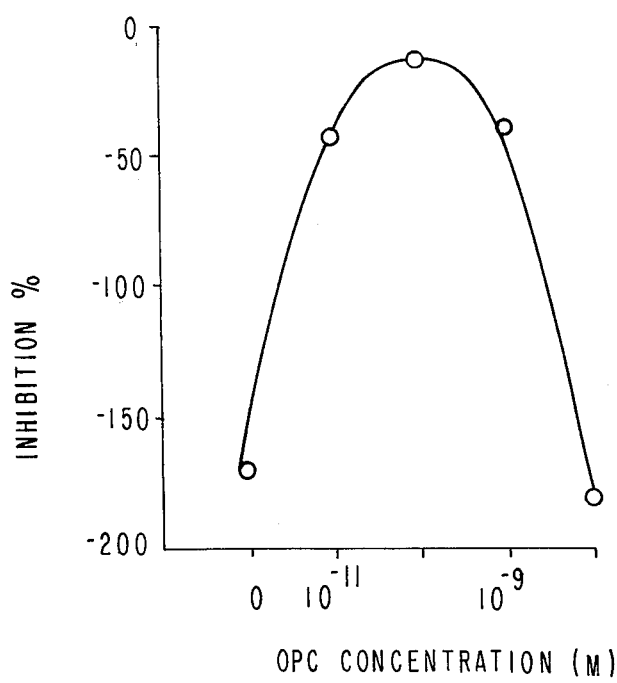
FIG. 4 shows the effect of OPC on platelet adhesiveness increased by adrenalin.

The results obtained are shown in FIG. 4, in which OPC was found to inhibit almost 100% of the platelet adhesiveness increased by the adrenalin at an OPC concentration of about $10^{-10}$M.

From the above results obtained in the foregoing Examples, it can be seen that the OPC according to the present invention inhibits platelet functions, i.e., aggregation property and adhesiveness at an extremely low concentration, i.e., from about $10^{-5}$ to about $10^{-11}$M, preferably from $10^{-8}$ to $10^{-10}$M. Thus, it is believed that the OPC can specifically inhibit platelet functions per se at a low blood level of OPC.

CLINICAL EXAMPLE

A patient suffering from angina pectoris orally received OPC at a daily dose level of 10 mg, and blood was taken 1 and 2 weeks after the commencement of the administration to determine platelet functions in the same manner as described in the foregoing Examples. The results obtained are shown in Table 1 below.

On the contrary, two patients (a) and (b) suffering from myocardiac infarction orally received acetylsalicylic acid at a daily dose level of 1.5 g. Blood was taken from the patient (a) 1 week after the commencement of administration and from the patient (b) 1 day after the commencement of administration, respectively. Platelet functions in each of the blood samples were determined in the same manner as described in the foregoing Examples, and the results obtained are shown in Table 2 below.

Table 1

Effect of OPC on Platelet Functions of Angina Pectoris (10 mg/day, p.o.)

|  | Before Adm. | 1 Week After Adm. | 2 Weeks After Adm. |
| --- | --- | --- | --- |
|  | (%) | (%) | (%) |
| Adhesiveness | 24 | 0 | 0 |
| Collagen-induced Platelet Aggregation | 82 | 48 | 57 |
| ADP-induced Platelet Aggregation | 50 | 0 | 45 |

Table 2

Effect of Acetylsalicylic Acid on Platelet Function of Two Patients with Myocardiac Infarction (1.5 g/day, p.o.)

| Patient (a) | Before Adm. | 1 Week After Adm. |
| --- | --- | --- |
|  | (%) | (%) |
| 39 |  |  |
| Collagen-induced Platelet Aggregation | 46 | 26 |
| ADP-induced Platelet Aggregation | 42 | 19 |
| Collagen-induced Platelet Aggregation | 35 | 31 |
| ADP-induced Platelet Aggregation | 36 | 48 |

From the results given in Tables 1 and 2 above, it can be seen that the effect obtained by administration of OPC at a level of 10 mg is comparable to that obtained by the administration of 1.5 g of acetylsalicylic acid, particularly, as far as the effect on platelet adhesiveness is concerned.

While the present invention has been described in detail and with reference to specific embodiments thereof, it will be apparent to those skilled in the art that many changes and modifications can be made therein without departing from the spirit and the scope thereof.

What is claimed is:

1. A method for preventing blood platelet aggregation and minimizing blood platelet adhesion comprising applying in vitro to blood or in vivo to mammals afflicted with thrombosis an effective amount of 5-(hydroxy-3-t-butylamino)propoxy-3,4-dihydrocarbostyril having the formula

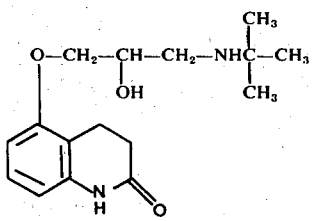

2. The method of claim 1 wherein the dihydrocarbostyril compound is present in the blood in an effective amount of from about $10^{-5}$ to about $10^{-11}$M.

3. The method according to claim 2, wherein said effective amount ranges from $10^{-8}$ to $10^{-10}$M.

4. A method for treating thrombosis to prevent blood platelet aggregation and to minimize blood platelet adhesion in a subject affected therewith comprising administering a therapeutically effective amount of 5-(hydroxy-3-t-butylamino)propoxy-3,4-dihydrocarbostyril having the formula

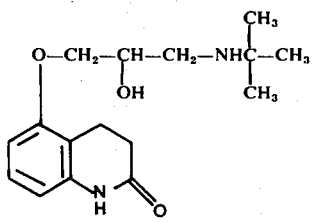

to said subject

5. The method of claim 4 wherein the dihydrocarbostyril compound is present in the blood in an effective amount of from about $10^{-5}$ to about $10^{-11}$M.

6. The method according to claim 5, wherein said effective amount ranges from $10^{-8}$ to $10^{-10}$ M.

7. The method according to claim 4 wherein 5 to 10 mg per subject per day is administered.

* * * * *